Figure 1:
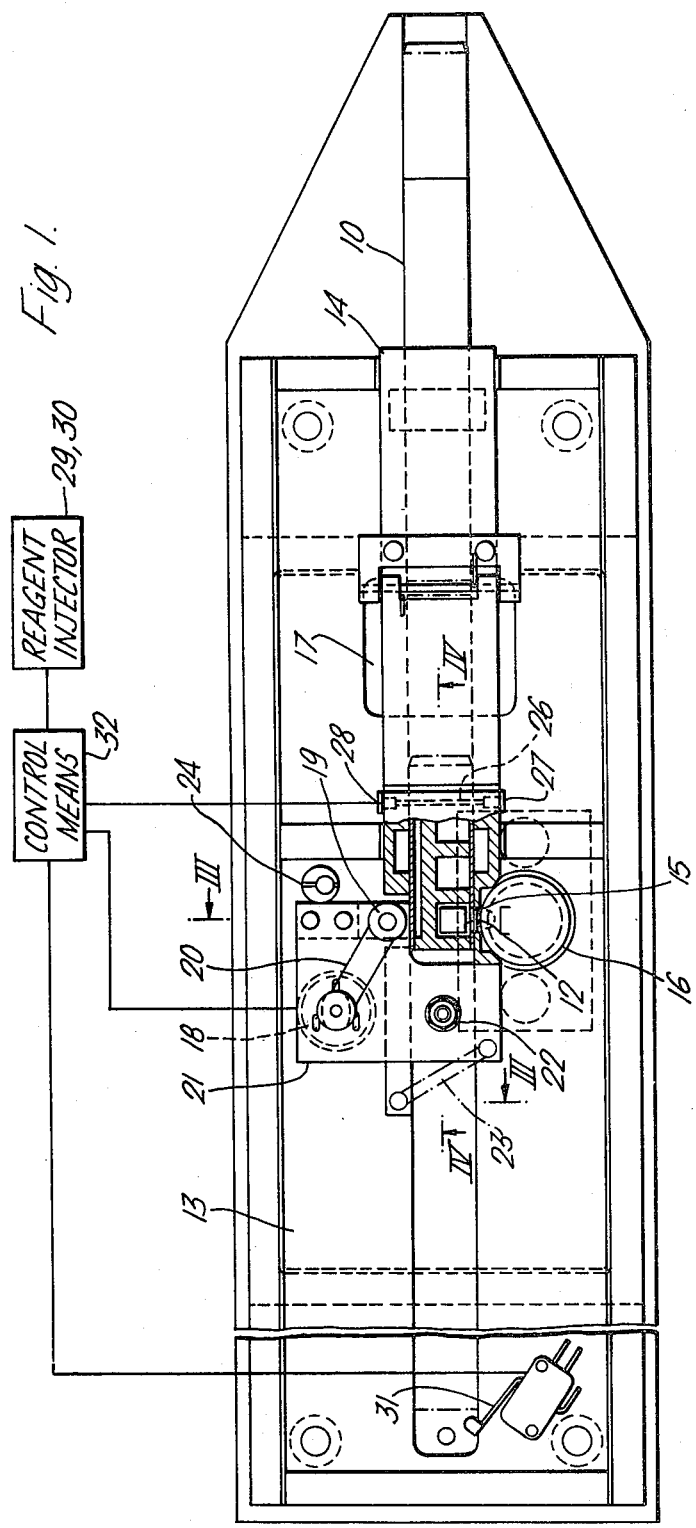

United States Patent [19]

Bunce et al.

[11] 4,366,118

[45] Dec. 28, 1982

[54] APPARATUS AND METHOD FOR LUMINESCENT DETERMINATION OF CONCENTRATION OF AN ANALYTE IN A SAMPLE

[76] Inventors: Roger A. Bunce, 117 Burberry Close, Bourneville, Birmingham; Timothy J. N. Carter, 14 Field Close, Sheldon, Birmingham B26 2NA; John H. Kennedy, 15 Dorset Rd., Edgbaston, Birmingham; Larry J. Kricka, 23 Kestrel Grove, Sellywood, Bourneville, Birmingham B30 1TQ; Thomas P. Whitehead, 70 Northumberland Spa, Warwickshire, all of England

[21] Appl. No.: 189,930

[22] PCT Filed: Jun. 13, 1979

[86] PCT No.: PCT/GB79/00102

§ 371 Date: Feb. 14, 1980

§ 102(e) Date: Feb. 14, 1980

[87] PCT Pub. No.: WO80/00100

PCT Pub. Date: Jan. 24, 1980

[30] Foreign Application Priority Data

Jun. 14, 1978 [GB] United Kingdom ............... 26924/78

[51] Int. Cl.³ .............................................. G01N 21/76
[52] U.S. Cl. ......................................... 422/57; 23/927; 356/244; 422/67
[58] Field of Search ....................... 422/52, 67; 23/927

[56] References Cited

U.S. PATENT DOCUMENTS

| | | | |
|---|---|---|---|
| 3,359,973 | 12/1967 | Hoffman | 422/52 |
| 3,504,259 | 3/1970 | Dalton | 318/265 |
| 3,520,660 | 7/1970 | Webb et al. | 23/253 |
| 3,523,737 | 8/1970 | Wood et al. | 356/180 |
| 3,532,469 | 10/1970 | Vicario | 23/253 |
| 3,813,168 | 5/1974 | Honkawa | 356/97 |
| 4,016,043 | 4/1977 | Schuurs et al. | 195/103.5 R |
| 4,281,387 | 7/1981 | Kraft | 422/67 X |

FOREIGN PATENT DOCUMENTS

| | | |
|---|---|---|
| 847694 | 9/1960 | United Kingdom . |
| 1402225 | 8/1975 | United Kingdom . |
| 1436182 | 5/1976 | United Kingdom . |
| 1447395 | 8/1976 | United Kingdom . |

OTHER PUBLICATIONS

Seitz et al. Analytical Chemistry, vol. 46, No. 2 (Feb. 1974).

Schroeder et al., Analytical Chemistry, vol. 48, No. 13 (Nov. 1976).

*Primary Examiner*—Sidney Marantz
*Attorney, Agent, or Firm*—Cushman, Darby & Cushman

[57] ABSTRACT

The apparatus comprises a movable member (10) which carries a plurality of cuvettes (11) containing material under test. Control means cause the member (10) to be moved to bring the cuvettes (11) successively into register with a photomultiplier (16), and in that position reagent is automatically added to a cuvette, giving rise to a luminescent reaction. Light from the reaction is detected by the photo-multiplier (16) and the resultant signal processed and recorded. The control means is triggered to stop the member (10), add reagent, record the signal from the luminescent reaction, and restart the member, from a photocell (28) which is illuminated through the member (10) only when a cuvette (11) is in register with the photomultiplier (16).

According to the method, sample material containing the analyte for determination is mixed with a known amount or concentration of the same analyte labelled with a substance which is capable of taking part in a luminescent reaction. The mixture is then reacted with a known amount of another substance capable of reacting with the analyte and giving rise to a luminescent reaction with the labelling substance. From quantitative observation of the light from the luminescent reaction the amount or concentration of the analyte in the sample may be deduced.

8 Claims, 4 Drawing Figures

APPARATUS AND METHOD FOR LUMINESCENT DETERMINATION OF CONCENTRATION OF AN ANALYTE IN A SAMPLE

It has been usual in, for example, medical and biomedical research and routine investigation and diagnostics, to measure the concentration in sample of various substances, hereinafter referred to as analytes, by causing such analytes to take part in a luminescent reaction with other predetermined substances, selected so that the output of luminescince in the reaction is uniquivocally related to analyte concentration. Measurements have been conducted more especially on substances present in body fluids, for example hormones, medicaments and blood constituents.

Publications in which such measurements have been described include UK Patent Specification No. 1461877 Wellcome Foundation; Belgian Patent Specification No. 856182 Maier; and the Proceedings of the First International Symposium on Analytical Applications of Bioluminescence and Chemiluminescence - Brussels Sept. 6-8, 1978.

Earlier methods have not always proved suitable for routine laboratory work in diagnostics, and the present invention has the potential for providing adequately for the needs of such work.

According to a first aspect of the invention, apparatus for luminescent determination of the amount or concentration of an analyte in a sample has a member having a plurality of cells, each adapted to contain a sample, and each having a window through which light can leave the cell; a test chamber adapted to receive at least part of the member containing a cell; a photodetector arranged to receive light emitted from a cell disposed at a testing station in said test chamber, and to provide an output signal dependent on said emitted light; and transport means adapted for moving the cells successively to the testing station.

According to another aspect of the invention there is provided a method of determining the amount or concentration of an analyte in a sample wherein there is carried out a luminescent reaction the light output from which is dependent on the said amount or concentration, and the light output being used to determine said amount or concentration, the analyte from the sample and a known amount of the same analyte labelled with a labelling substance being reacted with a specific reagent to produce a reaction product, and the amount or concentration of reacted or unreacted labelled analyte, the labelling substance being determinable, and hence the labelled analyte, by measuring the light output from a luminescent reaction in which the labelling substance takes part.

The term "specific reagent", used above, implies a reagent chosen to react with the particular analyte to be determined. For example, the analyte may be an antigen, in which case the specific reagent could be an antibody, or vice versa.

The luminescent reaction may be a chemiluminescent reaction or a bioluminescent reaction.

Figure 2:
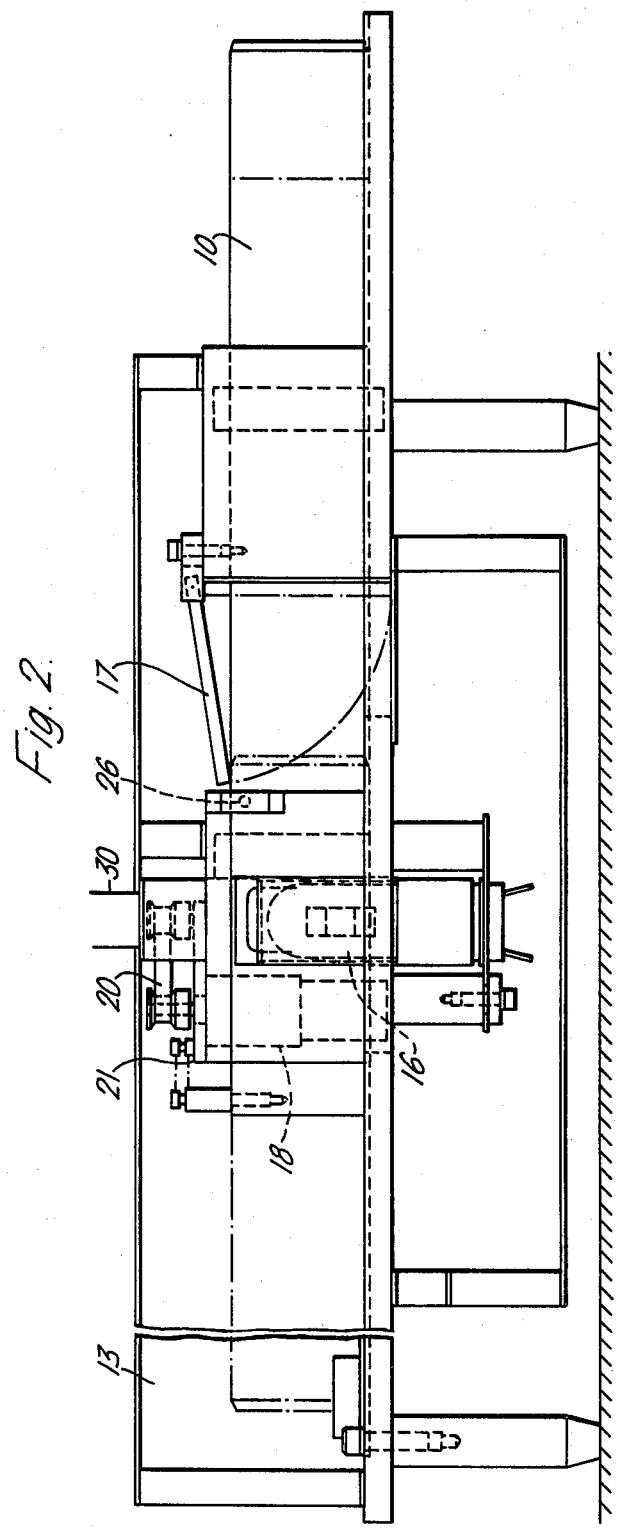
Figure 3:
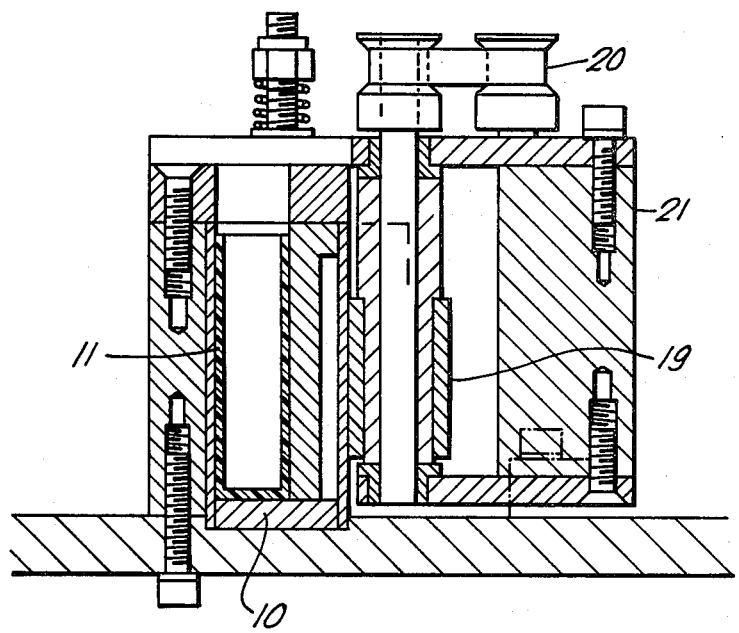
Figure 4:
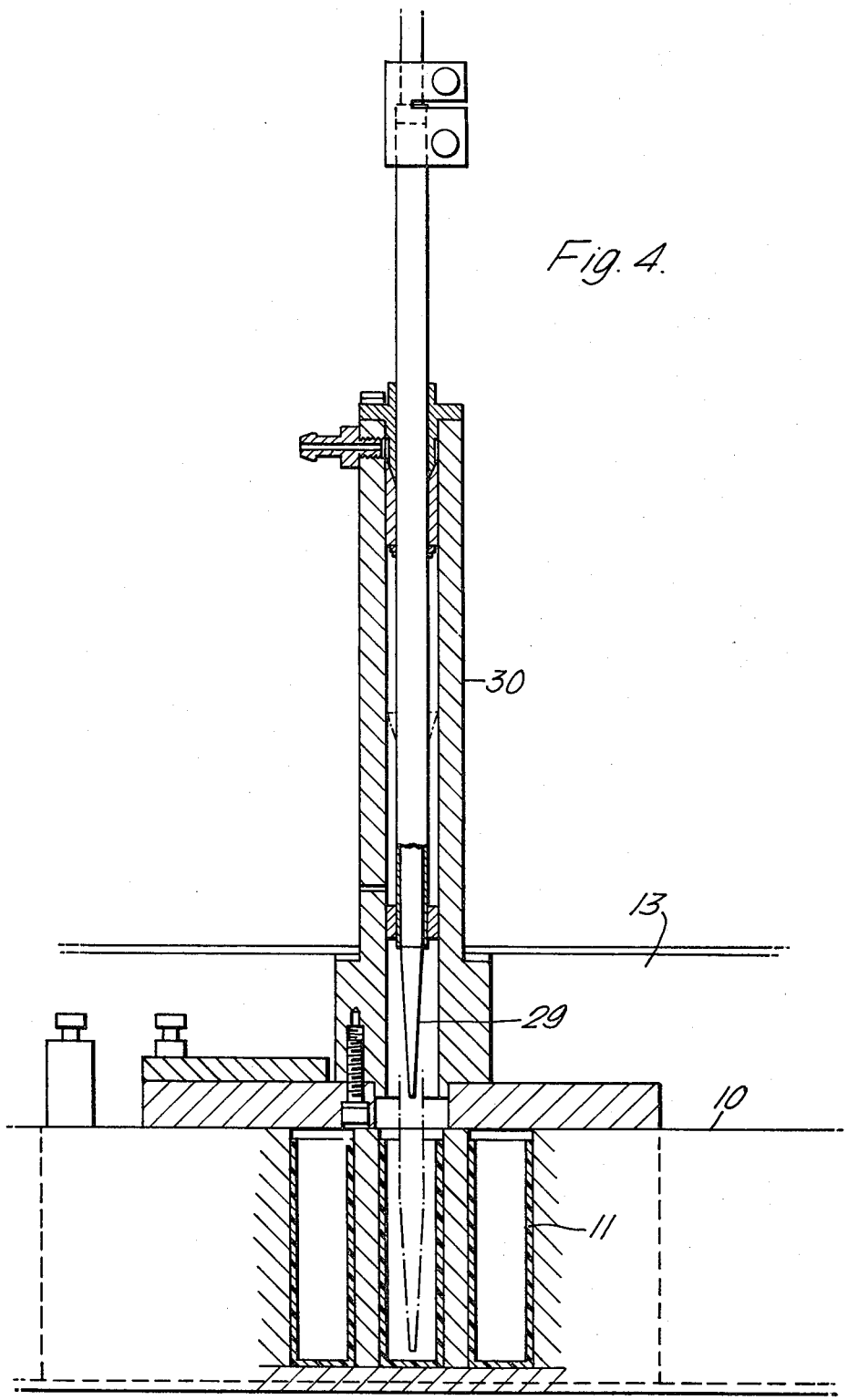

The invention will now be described, by way of example, with reference to the accompanying drawing wherein:

FIG. 1 shows a plan view of apparatus in accordance with the invention, an upper part of the apparatus being omitted, FIG. 2 shows a side elevation of the parts shown in FIG. 1, FIG. 3 shows a partial cross section on the line 3—3 of FIG. 1, and FIG. 4 shows a partial cross section on the line 4—4 of FIG. 1.

The apparatus may be used in the determination of the amount or concentration of an analyte in a liquid sample. The analyte may be an antigen, for example a protein, or it may be a nucleotide, for example nicotinamide adenine dinucleotide (NAD) or adencsine triphosphate (ATP) or a substrate from which one of these can be produced. In a case where the analyte is an antigen, the sample and a known amount of labelled antigen are reacted with an antibody for the antigen and the product of this reaction is separated, for example by precipitation, from the unreacted antigen. The labelled antigen is prepared by attaching to an antigen which is identical with the analyte a molecule which can participate in a luminescent reaction. The labelling molecule may be a luminescent reagent, for example luminol but is preferably an enzyme capable of catalysing a luminescent reaction. One example of such an enzyme is peroxidase.

The solution remaining after separation of the product of reaction of the antigen with the antibody contains both labelled antigen and analyte, the proportion being dependent upon the amount of analyte present in the original sample. Such solutions obtained from different original samples are placed in respective cells of the apparatus illustrated in the drawings.

The apparatus comprises a member in the form of a block 10 of aluminium or other material which is a good thermal conductor. The block has a number of cells for receiving respective solutions which are to be tested. In the particular example illustrated, each cell is defined by a commercially available element of transparent plastics material generally known as a cuvette. The cuvettes are received in respective pockets arranged in a row adjacent to one lateral margin of the block 10 and can readily be removed for cleaning, storage or disposal to waste, and replaced by fresh cuvettes. Adjacent to one wall of each cuvette, the block is formed with a respective aperture 12 through which light can escape from the cell.

The apparatus further comprises a test chamber 13 which can receive the entire block 10 in which the cuvettes 11 are supported. At one end of the chamber 13 there is an opening 14 through which the block 10 can be inserted into the chamber. At a testing station, there is in a side wall of the chamber a window or aperture 15 through which light emitted from a cell can leave the chamber and enter a photodetector mounted adjacent to a side wall of the chamber and overlying the aperture 15. The photo-detector is preferably a photo-multiplier tube 16. Near to the opening 14 light seals are provided in the chamber to prevent light entering the chamber between the block 10 and the walls of the chamber. A light trap is also provided between the aperture 15 and the seals at opening 14. The chamber is generally light-tight, except for the aperture 15.

A spring loaded flap 17 is arranged normally to close the chamber at a position between the opening 14 and the aperture 15 when the block 10 is absent from the chamber. This flap prevents ambient light entering the photo multiplier tube. When the block 10 is inserted into the chamber the flap 17 is pushed to an inoperative position illustrated in FIG. 2.

Transport means is provided for moving the block 10 along the chamber 13 in a stepwise manner to index the cuvettes 11 into the testing station successively. The transport means comprises an electric motor 18 which drives a rubber surfaced roller 19 through a belt and pulley drive 20. The motor and roller are mounted on a carrier 21 which can pivot about a vertical axis 22 and is urged by a spring 23 to move about its pivot in such a direction that the roller 19 is urged against a lateral surface of the block 10 when the latter is present in the chamber 13. The cam 24 serves as a stop to prevent excessive scraping action of the roller 19 on block 10 when the latter is inserted or extracted.

At a predetermined position relative to each cuvette 11 there is formed in the block 10 a respective transverse bore 26. For sensing the arrival of each cuvette at the testing station, there is provided in the chamber 13 at one side of the block 10 an infrared light source 27 and at the opposite side of the block a photo transistor 28. When a cuvette is situated at the testing station, in alignment with the aperture 15, the infra red light source and photo transistor are in alignment with a corresponding one of the bores 26. The motor 18 is a DC servomotor capable of positioning the block 10 precisely with a cuvette at the testing station.

For delivering a luminescent reagent into each cell there is provided a reagent injector comprising a tube 29 (FIG. 4) which is connected to an automatic dispensing pipette (not shown) and is mounted for reciprocation along a vertical path which extends upwardly from the testing station. The tube is secured to the piston of a pneumatic piston and cylinder unit 30 which can lower the tube from the rest position indicated in full lines in FIG. 4 to the injection position indicated by a chain line in FIG. 4 and then raise the tube to its rest position, it is entirely above the level of the cuvettes 11 and block 10. When in its injection position, it extends into a cuvette at the testing station to within a short distance of the bottom of the cell defined thereby.

Air is supplied to the piston and cylinder unit 30 via an electrically operated valve (not shown) which is connected in an electric circuit of control means 32, in itself of conventional kind. The photo transistor 28 and motor 18 also are connected in the circuit of the control means. The control means 32 is settable to establish a predetermined cycle time which may vary from one second to ten minutes. The control means provide a visual indication of the position of the block 10 to identify the particular cell which is aligned with the photo multiplier tube.

In a case where each solution to be tested contains an antigen labelled by the enzyme peroxidase or other suitable enzyme, a known quantity of the solution, together with a first luminescent reagent and, possibly, a diluent, is introduced into one of the cuvettes 11 whilst the block 10 is removed from the chamber 13. Solutions derived from other samples may similarly be introduced into the other cuvettes. The block is then vibrated to mix the solutions thoroughly and the solutions are brought to a predetermined temperature by temperature regulating means embedded in the block 10. The temperature regulating means may comprise, for example, a heating element, a circulating tube for cool or warm fluid, or a Peltier electric cooling or heating element; all controllable by thermostat. The block is then transferred to the chamber 13 and inserted into the chamber until it engages the roller 19. The control means of the apparatus is then energised to bring about cyclic operation of the apparatus to test the solution contained within each cell in turn. When a cell has been moved into the testing station, the tube 29 is lowered into that cell and a predetermined volume of a second luminescent reagent is injected into the cell at a velocity such that mixing of the liquids within the cell occurs rapidly. This enables the luminescent reaction to take place and light is emitted from the cell through the window constituted by the transparent wall of the cuvette and the aperture 12. The photo multiplier tube 16 provides an output signal dependent on the light emitted from the cell. After a selected interval has elapsed, the tube 29 is raised to its rest position, and the next cell is moved into the testing station.

In the case where the first reagent is hydrogen peroxide, the second luminescent reagent may be luminol. The concentration of the enzyme in each cell depends upon the amount of analyte in the sample corresponding to that cell. Variations in the amount of analyte in the different samples result in corresponding variations in the rate at which the luminescent reaction occurs within the different cells and this results in correspondingly different rates of light output from the cells.

Although it would be possible to use one of the luminescent reactants as a label on the antigen, we prefer to use the enzyme as a label. Since the amount of enzyme present does not decrease as the luminescent reaction proceeds, a relatively constant output is obtained from the photo multiplier, after an initial stage during which the output increases rapidly. Furthermore, the presence of a protein on the enzyme does not usually inhibit the catalytic action of the enzyme; whereas the presence of a protein on luminol results in steric hindrance or inactivation which reduces the rate of the luminescent reaction and therefore the sensitivity of the procedure to variations in the amount of analyte present in the initial sample.

The output from the photo multiplier tube 16 may be represented graphically by a chart recorder, integrated over the period during which light emitted from one cell is being sensed by the tube 16, or over a selected part of such period, or processed in any other manner.

The apparatus may be used in the determination of the concentration of ATP in a sample. ATP reacts with firefly luciferin in the presence of the enzyme firefly luciferase to produce adenosine monophosphate (AMP). Light is emitted when this reaction occurs. A predetermined volume of the sample containing ATP and a solution of firefly luciferase are placed in a cuvette 11 and mixed by shaking, the temperature of the solution being adjusted to a predetermined value. The cuvette, carried in the block 10, is then moved into the testing station where a predetermined volume of a solution of firefly luciferin is injected into the solution via the tube 29 in such a manner that the solutions are mixed quickly. The light emitted during the reaction is sensed by the photo multiplier tube 16, the output of which is used to determine the concentration of ATP in the sample. A suitably modified procedure may be used to determine the concentration in a sample of a substrate from which ATP can be produced.

The apparatus may also be used in the analysis of a solid sample, such sample being placed in a cuvette and there being added from the tube 29 a reactant which promotes a luminescent reaction of the sample.

A solid state electronic device or a film may be used as the photodetector in place of the photo multiplier tube.

Generally, we prefer to label the antigen, antibody or a specific binding protein with an enzyme which is capable of catalysing a luminescent reaction. Alternatively, the label could be a reactant which participates in a luminescent reaction or a precursor of such a reactant or a catalyst of a luminescent reaction. For example, an antigen could be labelled with an aliphatic aldehyde (e.g. tetradecylaldehyde, dodecylaldehyde) via a photochemical reaction of the aldehyde with 4-fluoro-3 nitrophenylazide and subsequent nucleophilic reaction of the reaction product with the antigen. The labelled antigen could then be determined by means of a bioluminescent reaction involving bacterial luciferase/FMN reductase.

For maintenance of uniformity of temperature between the contents of the different cells or cuvette 11, the following mode of operation of the apparatus has been found advantageous. The block 10 is inserted through the opening 14 to engage with the roller 19, by which it is moved fully and uninterruptedly into the test chamber 13 until it operates a limit switch 31, forming part of the control means 32 of the apparatus. Operation of this switch reverses the motor 18 to move the block 10 back out of the test chamber, following the aforementioned cyclic operation, to test the samples in each cuvette 11 in turn. In this way, the samples can be affected by ambient temperature only after they have been tested.

In this specification the term "light" implies electromagnetic radiation, not only of optical but of infra red and ultra violet wavelengths; and may extend from radio to X-ray wavelengths.

We claim:

1. Apparatus for luminescent determination of the amount or concentration of an analyte in a sample, comprising
    a block member including a plurality of cells, each cell being adapted to contain a sample, and each having a window through which light can leave the cell; a test chamber for mounting the block member containing at least one cell;
    a photodetector mounted to receive light emitted from a cell and disposed at a testing station in said test chamber to provide an output signal dependent on said emitted light;
    delivery means for delivering a predetermined amount of reagent into a cell at the testing station, said delivery means including a reagent injector mounted for reciprocal movement into and out of a cell to deliver reagent into the cell substantially at the bottom thereof; and
    transport means adapted for moving the cells successively to the testing station including settable control means for automatically controlling the transport means and delivery means to establish cyclic operation in which a cycle comprises moving a cell to the testing station, delivering reagent into the cell, detecting the light output from that cell for a predetermined period and finally moving the cell away from the testing station, the control means being actuated from photo sensitive means which is illuminated from an infrared light source through a bore in block member when any cell is at the testing station.

2. Apparatus according to claim 1 wherein the control means is arranged first to move the block member fully and uninterruptedly into the test chamber and then to move the block member out of the test chamber in accordance with said cyclic operation.

3. Apparatus according to claim 2 wherein each cell has a transparent wall portion which forms the window of the cell.

4. Apparatus according to claim 2 wherein each cell is defined by an element which is removable from said block member for cleaning, storage, or for disposal to waste.

5. Apparatus according to claim 2 wherein the transport means includes an electric motor driving the block member with a belt and pulley, and a rubber surfaced roller which bears on the block member.

6. Apparatus according to claim 3, 4 or 5 wherein the temperature of cell contents in the block can be regulated by temperature regulating means embedded in said member.

7. Apparatus according to claim 6 further comprising light-excluding means which prevents ambient light from entering the test chamber through any aperture therein.

8. Apparatus according to claim 7 wherein said light-excluding means includes a spring loaded flap coacting with the block member when said block member is at least partly in the test chamber.

* * * * *